United States Patent [19]

Crankshaw

[11] Patent Number: 5,034,004

[45] Date of Patent: Jul. 23, 1991

[54] INFUSION PUMP AND DRIVE SYSTEMS THEREFOR

[75] Inventor: David P. Crankshaw, Toorak, Australia

[73] Assignee: The University of Melbourne, Victoria, Australia

[21] Appl. No.: 427,121

[22] PCT Filed: Jun. 20, 1988

[86] PCT No.: PCT/AU88/00198

§ 371 Date: Oct. 23, 1989

§ 102(e) Date: Oct. 23, 1989

[87] PCT Pub. No.: WO88/10383

PCT Pub. Date: Dec. 29, 1988

[30] Foreign Application Priority Data

Jun. 19, 1987 [AU] Australia .............................. PI2644

[51] Int. Cl.[5] ........................ A61M 5/20; F16H 37/04

[52] U.S. Cl. ...................................... 604/154; 604/67; 128/DIG. 1; 128/DIG. 11

[58] Field of Search ................ 128/DIG. 1, DIG. 12, 128/DIG. 13; 604/65, 67, 151-155

[56] References Cited

U.S. PATENT DOCUMENTS

| | | | |
|---|---|---|---|
| 4,273,122 | 6/1981 | Whitney et al. | 128/DIG. 1 |
| 4,274,409 | 6/1981 | Bush | 604/153 |
| 4,397,642 | 8/1983 | Lamadrid | 128/DIG. 13 |
| 4,424,720 | 1/1984 | Bucchianeri | 128/DIG. 1 |
| 4,627,835 | 12/1985 | Fenton, Jr. | 128/DIG. 1 |
| 4,741,732 | 5/1988 | Crankshaw et al. | 604/155 |
| 4,767,406 | 8/1988 | Wadham et al. | 604/155 |
| 4,838,857 | 6/1989 | Strowe et al. | 128/DIG. 12 |
| 4,846,797 | 7/1989 | Howson et al. | 128/DIG. 1 |

FOREIGN PATENT DOCUMENTS

| | | | |
|---|---|---|---|
| 0866461 | 8/1941 | France | 604/153 |

*Primary Examiner*—Stephen C. Pellegrino
*Assistant Examiner*—Ralph A. Lewis
*Attorney, Agent, or Firm*—Rothwell, Figg, Ernst & Kurz

[57] ABSTRACT

A drug infusion pump having a drive system including a drive motor (49), a worm gear (53) on the output shaft of said motor, a worm wheel (55) meshing with said worm gear (53) and constructed to drive an output reduction gear (60) and clutch means (62) associated with said output gear (60) for disengaging drive to a drive head (61) engaged by a drive belt (83) which is permanently connected to a syringe actuator (7) to cause controlled infusion of the contents of a syringe under the control of a central control system including a microprocessor (20) and programmable memory means (21 and 23) which determine the manner in which the infusion is performed. A syringe clamping arm (5) is associated with a potentiometer (24) which provides to the controller diameter information regarding the syringe. The programmable memory means (23) includes data relating to one or more standard syringe sizes to enable automatic operation on insertion of a standard syringe. In the event that a non-standard syringe is to be used, the infusion pump may be simply programmed to allow such non-standard syringes to be used.

7 Claims, 4 Drawing Sheets

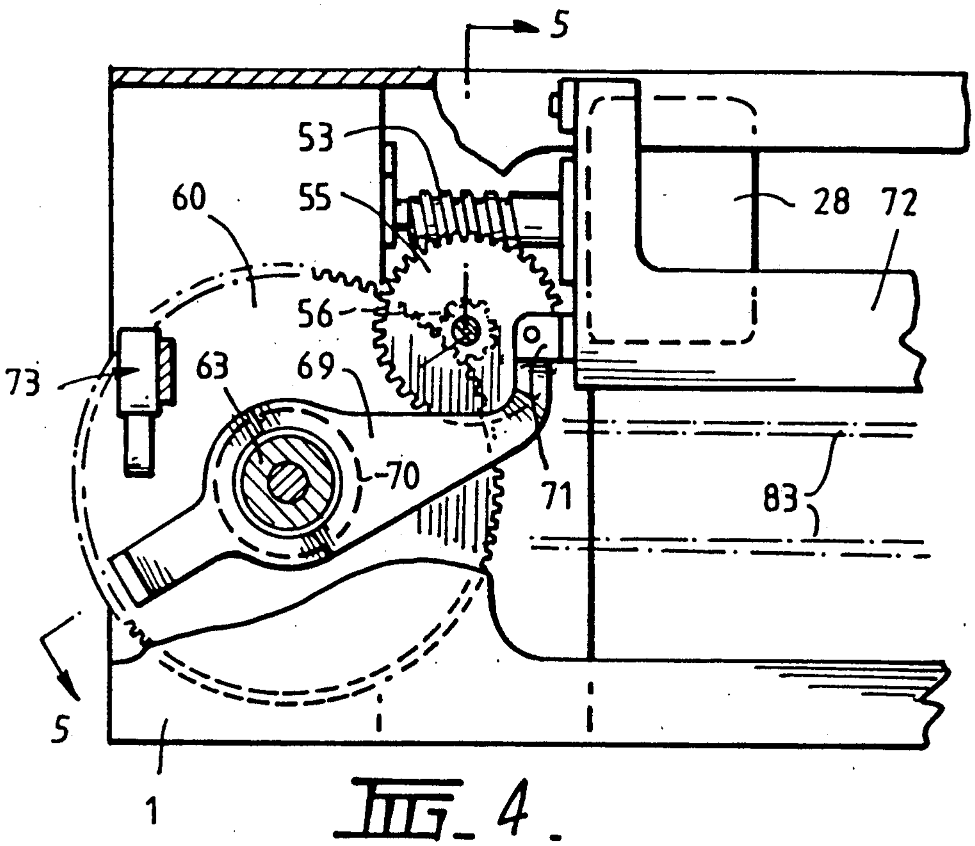
FIG. 4.
FIG. 5.
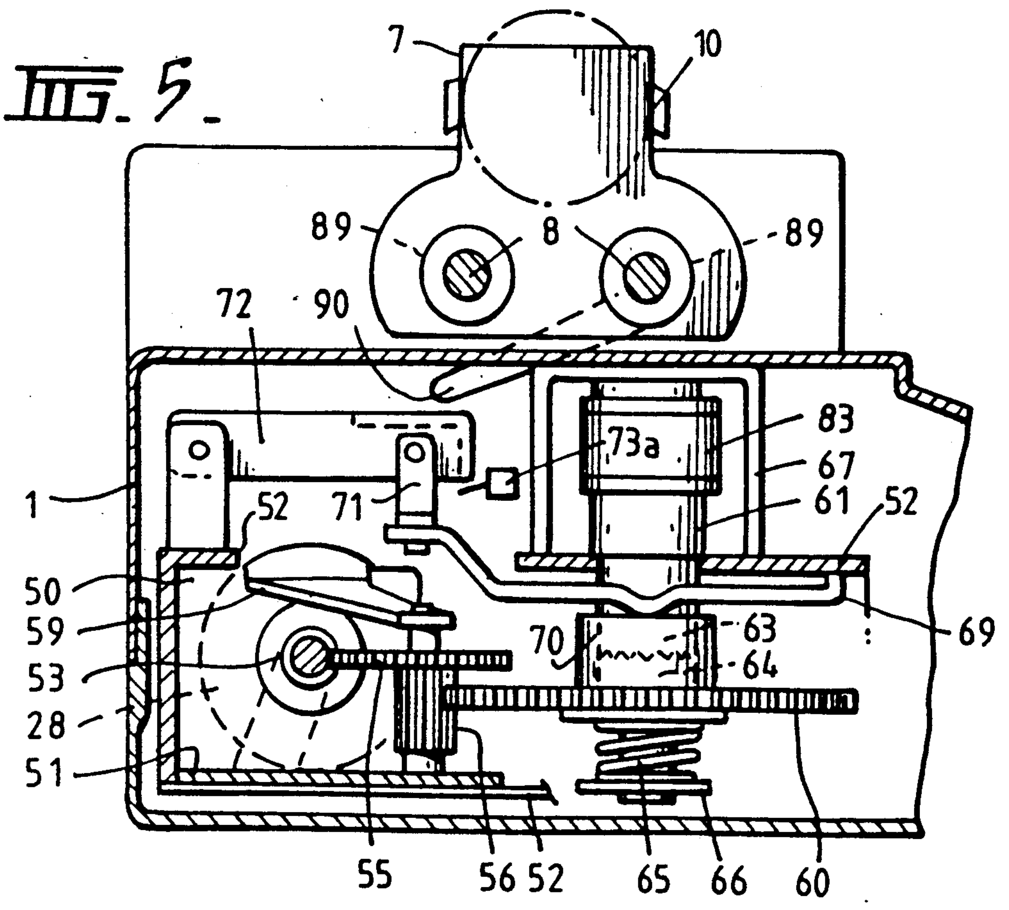

INFUSION PUMP AND DRIVE SYSTEMS THEREFOR

FIELD OF THE INVENTION

This invention relates to improvements in pumps for the delivery of drugs and other fluids in metered quantities.

BACKGROUND OF THE INVENTION

In our prior U.S. Pat. No. 4,741,732 Crankshaw et aly, the disclosure of which is incorporated herein by reference, we described a drug infusion pump having a drive system including a drive wheel on the output shaft of a DC gear motor biased to engage a resilient drive ring on a drive wheel which transmits drive to a drive head engaged by a toothed drive belt. While the described drive system was acceptable for an experimental pump designed to establish the workability of the drug infusion control system described in the application, subsequent consideration of the drive system revealed that it had certain shortcomings which made it unsuitable for commercial application.

In particular, it was found that the drive system had a tendency to reverse the drive motor due to recoil caused by deformation of the syringe, flexing of the support structure, elasticity in the drive belt and slackness in the drive system generally. Although the controller was able to successfully monitor such backlash and thereby monitor the actual position of the syringe plunger, direct computation of pump speed and plunger position was found to be most desirable. Furthermore, the achievement of lower drive speeds without recoil as well as wide speed ranges was found to be substantially impossible to achieve using the described drive system.

While more positive drive systems for the delivery of a drug from a syringe have been proposed, for example, see U.S. Pat. No. 4,407,659, such systems suffer from a number of disadvantages, including the inability to conveniently disconnect the drive to enable rapid positioning of the syringe actuator as well as the inability to achieve low delivery rates in combination with high delivery rates. As has been explained in the prior patent referred to above, drug infusion control systems often require very rapid delivery rates in the early stages of the control delivery in combination with very low rates of drug delivery in the latter stages of the infusion. The prior art drive systems do not allow the achievement of such delivery regimens.

A wide range of controlled infusion pumps which are adapted to deliver drugs from a syringe are currently available and are widely use for a number of purposes in the medical field. Several of these pumps have a limited ability to "recognize" one or more standard syringe sizes (Atom 235 and Terufusion STC-521). Other pumps are highly programmable to accept a range of different standard syringes (Medfusion Systems—Model 1001, Vial Medical Programme 3 and Sky Electronics—PS2000). However, none of the programmable infusion pumps currently available are able to recognize when a non-standard syringe is fitted to the pump or have the ability for the operator to input data relating to a non-standard syringe on the basis of which the delivery of fluid from such a syringe may be accurately controlled. The danger flowing from the above inability is the possibility of inaccurate pumping in the event that a non-standard syringe is used. At least some of the above pumps will operate when a non-standard syringe is inserted on the assumption one of the programmed standard syringes has in fact been inserted. The dangers of this type of operation are clearly obvious.

SUMMARY OF THE INVENTION AND OBJECTS

It is a first object of the present invention to provide an improved drive system for a drug infusion pump by means of which the above deficiencies may at least in part be overcome.

It is a second object of the invention to provide a controlled pump for the delivery of fluids from syringes in which the difficulties associated with the use of non-standard syringes is reduced.

In relation to the first object, the present invention provides a drive system for an infusion pump comprising a drive motor, a worm gear attached to the output shaft of said motor, a worm wheel meshing with said worm gear and constructed to drive an output reduction gear, and clutch means associated with said output gear for disengaging drive to a drive member associated with said output gear, said drive member being adapted to operate an infusion pump.

In a preferred embodiment, said worm wheel is preferably provided with a splined hub or pinion with which said output reduction gear meshes, said clutch means being interposed between said output gear and said drive member, and clutch operating means positioned between said frame and said clutch means and adapted to move said output gear downwardly along said splined hub when said clutch is disengaged.

The clutch means is preferably a spring loaded sprag clutch which is adapted to disengage automatically when the force applied to said output gear exceeds a predetermined amount.

In a particularly preferred form of the invention, the drive motor and worm wheel are supported by a separate frame member which may be readily detached from said frame as a unit for convenient adjustment, repair or replacement.

It will be appreciated from the above that the required drive with reduction and drive disengaging clutch is achieved in a particularly compact arrangement which has the ability to provide a wide range of drive speeds whilst still maintaining acceptable dimensions.

In relation to the second object, the invention provides a pump for the delivery of controlled amounts of fluid from a syringe having a body and a plunger, comprising means for receiving and locating the body of the syringe, syringe actuator means for engaging the plunger of the syringe held by a said receiving and locating means, means generating electrical signal representing the position of said syringe actuator means, drive means connected to said actuator means to move the plunger into said syringe to deliver said fluid, said drive means including a permanently maintained connection between said drive means and said means for generating said electrical signal relating to the position of said actuator means, a movable arm for contacting the body of the syringe when held by said receiving and locating means, means for generating an electrical signal on movement of said arm into engagement with said syringe body to provide a signal representative of the diameter of the syringe, programmable means for holding diameter data relating to one or more syringes, logic means for determining whether the value of the electrical signal relating to diameter is a programmed value and for creating signals responsive to that determination, means responsive to a said signal representative a negative determination for allowing the inputing of data to said pump controlling means by movement of said actuator means into engagement with the plunger of a fully expended syringe of the required volume, followed by engagement of the actuator means with the plunger of a full syringe of the required volume, and means for calculating from that information and the known volume of the desired syringe a delivery factor which is stored in memory means for use by the control means to control the delivery of the fluid contained in the syringe at a predetermined delivery rate.

It will be appreciated from the above that an operator may quickly calibrate the pump to control the delivery of fluid for any syringe, even when an operation is in progress. This is important in the case of the infusion of anaesthetics since some drugs allow the patient to resume consciousness in a very short period of time, e.g. 2 minutes.

BRIEF DESCRIPTION OF THE DRAWINGS:

One preferred form of the invention will now be described with reference to the accompanying drawings in which:

FIG. 4 is a fragmentary plan view taken along the line 4—4 in FIG. 3, and

FIG. 5 is a sectional end elevation taken along the line 5—5 in FIG. 4.

DESCRIPTION OF PREFERRED EMBODIMENT

Figure 1:
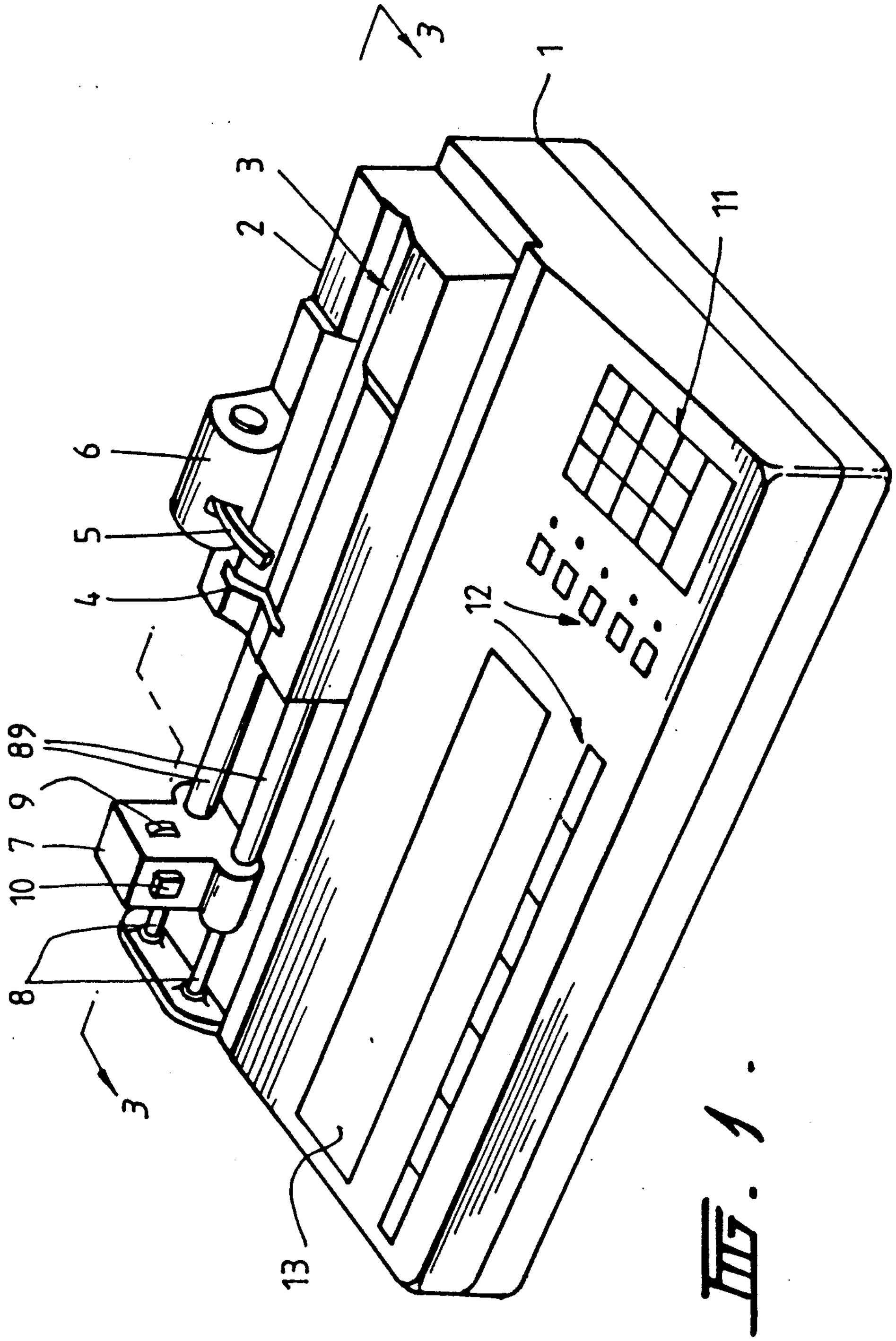
FIG. 1 is a perspective view of a pump embodying the invention.

Referring first to FIG. 1 of the drawings, the infusion pump embodying the present invention will be seen to comprise a casing 1 within which the drive system embodying the invention is located, the casing 1 including a syringe cradle 2 having a centrally located groove 3 for locating the body of a syringe S (FIG. 3), and a slot 4 for receiving and locating the syringe flange. The syringe S is held in position in the groove 3 by means of a spring loaded syringe clamping arm 5 which is pivotally mounted within a housing 6 extending upwardly from the cradle 2. A syringe actuator 7 is mounted on a pair of tubes 89 for sliding movement along a pair of guide rods 8 supported by the casing 1 and is driven by a driving mechanism located within the casing 1, and which will be described in greater detail below, to engage the plunger of the syringe S to cause the fluid contained in the syringe to be administered in a manner controlled by the central controlling system (FIG. 2) of the pump. The actuator 7 carries a proximity micro switch 9 and a clutch releasing button 10. The proximity microswitch 9 detects when the actuator 7 initially engages the plunger of the syringe so that the pump controller is made aware that contact with the plunger has occurred. The clutch releasing button 10 disengages the drive motor from the drive system to allow the actuator to be freely moved between its operating extremities for the purposes described further below.

The infusion pump casing 1 includes a key pad 11 including the usual array of numerical keys, an enter key, a clear key and a stop key. In addition, several other keys 12 are also provided on the front panel, including:

BATT TEST—enables the charged state of the battery to be ascertained. An associated LED indicates if charging is in progress.

ALARM—enables an alarm to be cancelled. An associated LED flashes when the alarm is tripped.

RUN—enables operation of the pump to commence. An associated LED illuminates when the run button is pressed.

BOLUS—causes bolus infusion, overriding the control program and causing infusion at a rate approximately equal to manual infusion. Again a LED illuminates when the bolus key is pressed.

STOP—stops the pump.

ASSIST—causes the interaction assistance programme to operate.

YES—enables a positive reply to the input.

NO—enables a negative reply to the input.

A liquid crystal diode (LCD) display panel 13 capable of displaying alpha numeric messages for the information of the operator in the manner described below is also provided.

Figure 2:
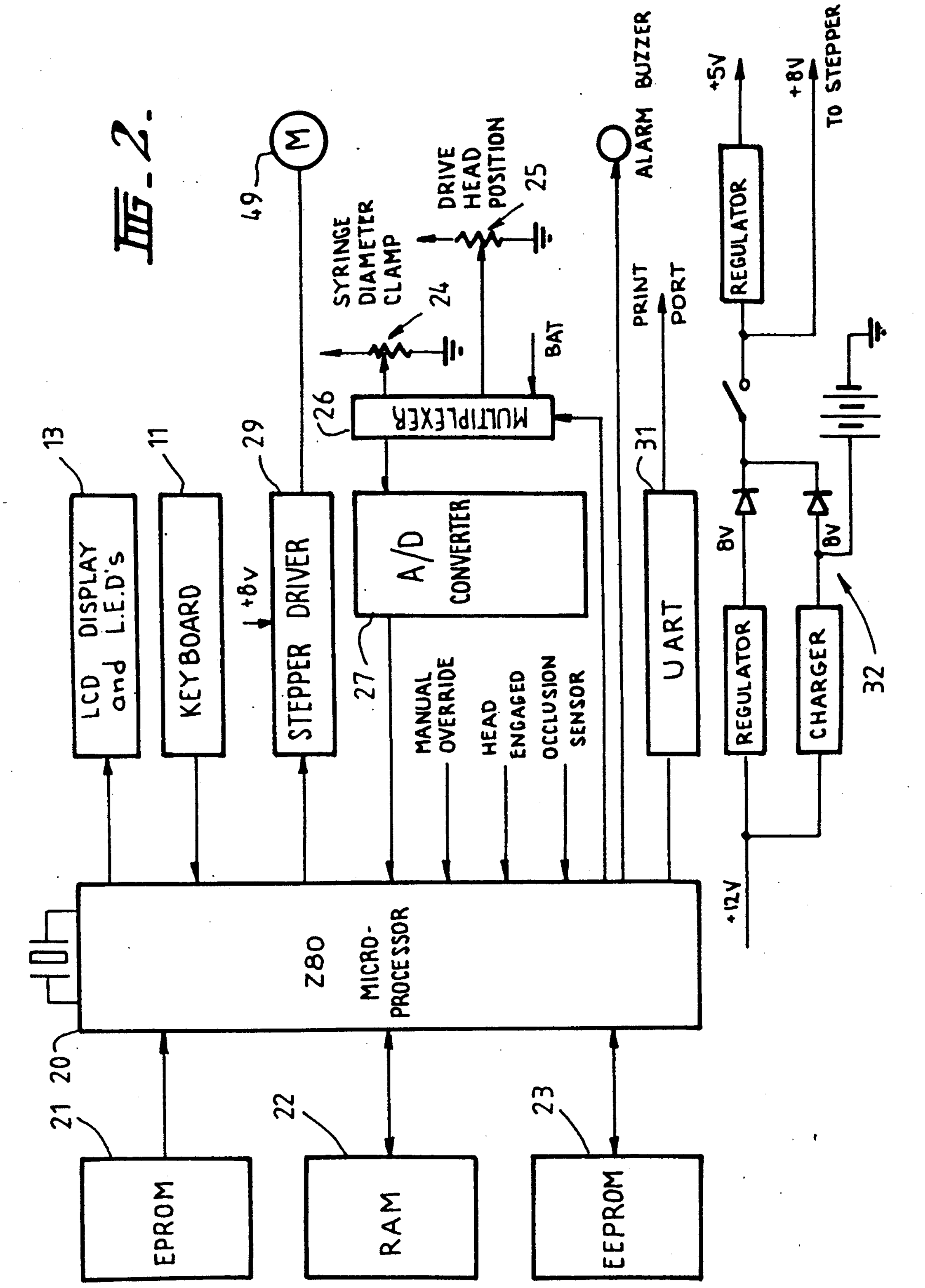
FIG. 2 is a schematic block diagram of the control system for the pump.

Referring now to FIG. 2 of the drawings, a block diagram of the pump controller circuitry is shown. The central microprocessor 20 is typically a Z80 type and is under the control of EPROM 21, RAM 22, EEPROM 23, a key pad 11 and a clamping arm potentiometer 24 and a syringe actuator position potentiometer 25, via multiplexer 26 and analog to digital converter 27. The controlling microprocessor 20 in turn controls the operation of a drive stepper motor 28 via a stepper driver circuit 29, the LCD display 13, an alarm buzzer 30 and a printer (not shown) via UART 31. The stepper drive circuit 29 is supplied by a power supply 32 which provides a regulated 5 volt output and an eight volt output for the stepper driver from a chargeable battery.

The EPROM 21 contains the variable programmed information on which the pump controller operates, including a series of drug infusion profiles relating to various drugs to be infused. In this regard, reference is made to the prior patent referred to above where the drug infusion profiles and the method of derivation thereof are fully described. Further description of the profiles will not be provided since the present invention is concerned primarily with the drive system for the infusion pump and the basic control system therefor. The RAM 22 constitutes the active memory of the control microprocessor 20 while the EEPROM 23 contains the fixed program data, and is capable of storing data relating to the position of the clamping arm 5 when syringes S of predetermined volumes are loaded into the cradle 2.

The controlling microprocessor 20 also receives electrical signals from microswitches which detect manual disengagement of the clutch, contact between the micro switch 9 and the plunger of the syringe S and unintended disengagement of the clutch caused by the occurrence of an occlusion preventing infusion.

Figure 3:
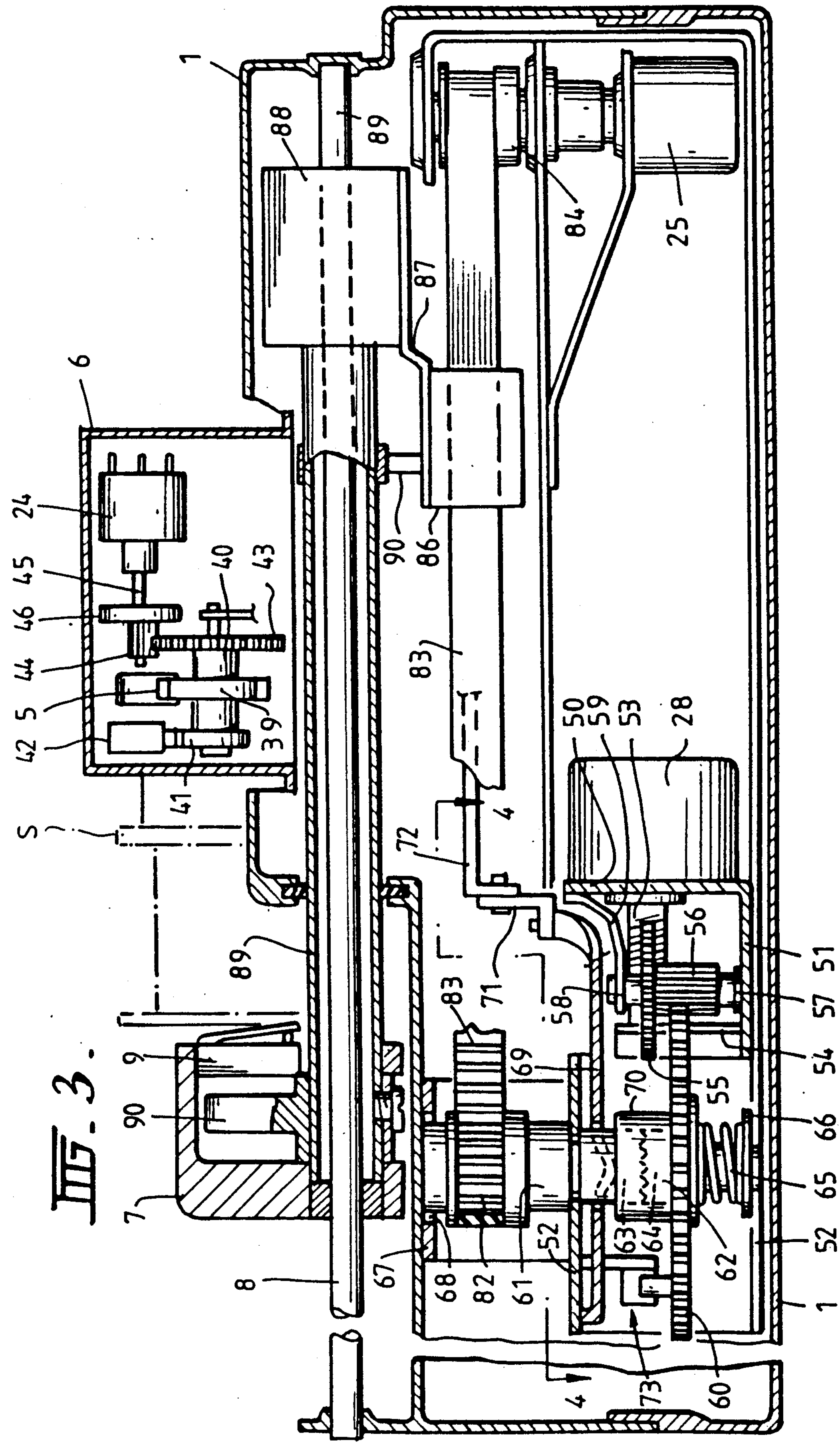
FIG. 3 is a fragmentary illustrative sectional elevation of the pump of FIG. 1 taken along the nominal line 3—3 in FIG. 1.

Referring now to FIGS. 3 to 5 of the accompanying drawings, the syringe clamping arm 5 extends from a support 39 carried by a rotatably mounted shaft 40 supporting a notched cam 41 which is positioned to operate an on/off microswitch 42 when the clamping arm 5 is moved from its rest or lowest position to actuate the control system for the pump. The support is in the form of a cam which bears against a spring loaded lever (not shown) to supply a biasing force which holds the clamping arm 5 in engagement with a syringe carried by the cradle 2. The support 39 is arranged to be in the over-center position when the clamping arm 5 is raised to its highest position. This enables the operator to position the clamping arm 5 at its highest point to enable loading of a syringe into the cradle 2.

The shaft 40 further carries a gear wheel 43 which meshes with a pinion 44 carried by the shaft 45 of the potentiometer 24. In this way, the full angular movement through about 35 degrees of the clamping arm 5 is amplified by the gear ratio of the gear 43 and pinion 44, which is usually about 4:1 or 5:1. Thus, a very small variation in the position of the clamping arm 5 produces a readily discernible change in the resistance of the potentiometer 24 thereby resulting in a change in the voltage signal delivered to the multiplexer 26.

The shaft 45 also carries a hair spring or watch spring 46 which has one end anchored to the casing 6 and the other end anchored to the shaft 45. The spring biases the pinion 44 in the required direction to prevent any backlash between the gears 43 and 44 being transmitted to the potentiometer 24.

The shape of the clamping arm 5 is selected so that most syringes in the range 10 to 50 ml can be accommodated in the syringe cradle 2, an approximately straight line relationship exists between the diameter of the syringe and the resistance of the potentiometer 24. In this way, the position of the clamping arm 5 is able to produce a voltage signal which provides an indication to the controlling computer 20 of the diameter of the syringe.

In the present embodiment, clamping arm potentiometer voltage or "diameter" information corresponding to four selected syringe sizes, such as, 10, 20, 30 and 50 ml, may be stored in the EEPROM 23 either before sale, during sale or after sale. Thus, when a selected syringe is loaded into the cradle 2 and the clamping arm 5 is lowered into engagement with the body of the syringe, a diameter voltage signal is generated by the potentiometer 24 and is transmitted via the multiplexer 26 and the analog to digital converter 27 to the central controlling microprocessor 20. This diameter signal is compared with the programmed diameter information contained in the EEPROM 23, which will usually be in the form of a look-up table, and if the diameter signal corresponds to one of the standard diameters within a reasonable tolerance such as ±2.5%, the controller 20 will cause the corresponding volume of that syringe to be displayed on the LCD display 13 so that the operator may confirm that the volume displayed is the correct volume of the syringe which has been inserted by pressing the YES button. Once confirmation has been entered by the operator, the pump is ready to operate according to a selected infusion rate profile in the general manner described in the prior patent referred to above.

In the event that a syringe for which the pump has not previously been calibrated (hereinafter "non-standard") is inserted into the syringe cradle 2, the diameter signal generated by the potentiometer 24 will not correspond to any one of the programmed diameters and the controller must then be manually programmed or recalibrated to enable operation using this non-standard syringe. Before the describing the manner of programming the controller to accept a non-standard syring, it is appropriate to further describe the drive system embodying the invention with reference to FIGS. 3 to 5 of the drawings.

The drive system comprises the stepping motor 28, which is horizontally mounted on a vertical support plate 50 having a horizontal portion 51 which is attached to the frame 52 which supports the cover 1. In the present embodiment, the stepper motor 28 is an ESCAP step motor P310, which has been found to be particularly suitable for the present purpose, and superior in operation to other stepper motors. While the use of a stepper motor, and particularly the above stepper motor, is particularly preferred since it enables highly accurate and rapid positioning of the drive system and therefore highly accurate and fast operation of the infusion pump, it should be appreciated that other forms of motor may be used to achieve acceptable results.

A worm gear 53 is fixed to the output shaft of the stepper motor 28 and is supported by a bearing plate 54 attached to the plate portion 51. The worm gear 53 meshes with a worm wheel 55 having a splined hub or pinion 56, the worm wheel 55 and pinion 56 being supported in a bearing 57 mounted on the frame 52 and a bearing 58 mounted in an overlying support plate 59 attached to the plate 50.

The support plate 50 and the frame portion 52 are in the preferred embodiment formed as a removable unit, to enable the motor 50, worm gear 53 and the worm wheel 55 to be separated as a unit to enable easy adjustment, repair or replacement.

An output reduction gear 60 meshes with the splined hub 56 and is drivingly attached to a drive head 61 via a sprag clutch 62. The sprag clutch 62 is of known construction and includes interengaged tooth elements 63,64 normally held in engagement with each other by means of a compression spring 65. The biasing force applied by the compression spring 65 is adjustable by means of packing washers 66 to vary the load at which the clutch 62 will automatically disengage when an undesirable over-pressure develops in the infusion line for the syringe S.

The drive head 61 is supported by the frame 52 and by a saddle frame 67 carrying a bearing 68 supporting the uppermost end of the drive head 61.

The sprag clutch 62 is also manually releasable by moving the lower most toothed element 64 against the action of the spring 65 by means of a lever arm 69 positioned between the frame 52 and an actuating sleeve 70 surrounding the clutch elements 63,64. The lever 69 is connected via a linkage 71 to a pivoted bar 72 which is pivoted by operation of the clutch release button 10 carried by the syringe actuator 7. The mechanism for achieving clutch release is essentially as described in the prior patent referred to above, although only one tube is used to transmit the clutch releasing movement.

The button 10 is positioned to engage a radial arm 90 connected to one of the tubes 89 surrounding guide rods 8. As described in greater detail in the prior patent, the tube 89 is rotatable within the actuator 7 (and within slider 88) and carries a drive release cam 90 which is positioned to engage the pivoted bar 72 when the tube 89 rotates in response to movement of arm 90 caused by manual depression of button 10.

A microswitch 73 is positioned between the frame 52 and the uppermost face of the output gear 60 so that an electrical signal is created whenever the sprag clutch 62 is partially or fully disengaged. While the microswitch 73 is in the present embodiment mounted on the output gear 60, it may be more conveniently located within the sprag clutch by itself. Furthermore, in order to distinguish between clutch disengagements caused by operation of the clutch release button 10 and clutch disengagements caused by clutch overload, such as would occur in the event of an occlusion, a further microswitch 73*a*is positioned adjacent to the pivoted bar 72 to detect operation of the clutch release mechanism before clutch release occurs. These different inputs to the microprocessor 20 are labelled "manual override" and "occlusion sensor". The input labelled "head engaged" inputs signals generated by the microswitch 9.

The drive head 61 includes a central toothed portion 82 which is drivingly engaged by a toothed drive belt 83 which engages a further drive head 84, similar to the drive head 61, mounted for rotation at the opposite end of the frame 52. The shaft of the drive head 84 is connected to a potentiometer 25 by means of which the position of the drive belt 83 is accurately monitored at all times. The drive belt 83 is permanently connected to syringe actuator 7 by means of a belt clamp 86 having a connector plate 87 which is in turn attached to a slider 88 connected to the syringe actuator 7 by a pair of tubes 89, the assembly being slidably mounted on the guide rods 8 carried by the casing 1 and the syringe cradle 2. In this way, a permanent driving connection is effected between the drive belt 83 and the syringe actuator 7, which driving connection is maintained irrespective of release of the sprag clutch 62 by means of the clutch release button 10. Thus, the position of the syringe actuator 7 is always known by the central controlling computer 20 since the voltage signal generated by the potentiometer 25 is fed to the microprocessor 20 via multiplexer 26 and analog to digital converter 27 whereby the position of the syringe actuator 7 and the distance it has travelled during any particular time period may be determined by the microprocessor 20.

It will be appreciated from the above that since a permanent driving connection is maintained between the drive belt 83 and the syringe actuator 7, the potentiometer 25 is at all times able to accurately sense the position of the syringe actuator 7, even where the drive clutch 62 is disconnected by means of depression of the button 10 and the syringe actuator 7 is moved freely along its guide rod 89 to perform a manual infusion or to program the controller to operate with a non-standard syringe.

As described above, the controller will detect the presence of a non-standard syringe in the syringe cradle 2 and will advise the operator via the LCD display 13 that programming is required before infusion may proceed. To program for a non-standard syringe, an empty syringe of the required volume is first loaded into the syringe cradle 2 and the clamping arm 5 lowered. The syringe actuator 7 is then slid along its guide rod 89 after releasing the clutch by means of button 10. The controller will then move the syringe actuator 7 until the microswitch 9 closes indicating that contact with the syringe plunger has occured. In this way the position of the syringe actuator 7 required to empty the desired syringe is indicated by the potentiometer 25 and the controller 20 receives this data via the multiplexer 26 and the analog to digital converter 27. The empty syringe is then removed and the syringe actuator 7 returned to its rest position. A full syringe is then loaded into the syringe cradle 2 and the clamping arm 5 lowered. The syringe actuator 7 is then advanced either manually, or under the action of the controller until the microswitch 9 contacts the syringe plunger. The starting position of the syringe actuator 7 prior to infusion occurring is then input to the controller 20 from the potentiometer 25. After this procedure is completed, the controller causes the LCD display 13 to request the operator to input the volume of the non-standard syringe whereupon the necessary delivery factor is calculated by dividing that volume by the distance measurement derived from the data relating to the respective positions of the syringe actuator 7 described above. The controller is then ready to perform the desired infusion profile using the last programmed non-standard syringe. In the present embodiment, only four calibrations may be stored in the look-up table, and if a further non-standard syringe is to be used, the data relating to that syringe will replace one of the previously input 'diameters'. Of course, the ability to store syringe 'diameters' may be expanded if desired although it is currently thought that four should be sufficient.

A typical series of operator prompts displayed on the LCD display 13 for a range of modes of operation will now be described to assist in a more complete understanding of the embodiment described above.

When the syringe clamping arm 5 is initially lifted from its rest position, microswitch 42 causes the controller to be powered up and the LCD display 13 displays the message:

LOAD FILLED SYRINGE AND LOWER CLAMP

If the syringe is a "standard" syringe, that is, one which has previously been calibrated and has its "diameter" reading in the look-up table contained in EEPROM 23, and assuming the syringe is a 60 mL syringe containing 50 mL of fluid, the display will register the message:

ESTIMATED VOLUME mL 50.00
IS THIS CORRECT?
YES/NO

If the operator is satisfied with the estimated volume, and presses the YES button, the display 13 will register:

VOLUME mL 50.00
IS THIS A NEW INFUSION?
YES/NO

If a new infusion is required, the operator presses the YES button and the display 13 reads:

FIXED OR PROGRAMMED?

If the operator selects FIXED, the display 13 will request the required rate to be input using the key pad 11. If the operator selects programmed, the display 13 requests the operator to input the desired drug and patient data in a manner similar to that described in the prior patent referred to above.

In the event that the estimated volume reading referred to above is incorrect, the following display appears:

ESTIMATED VOLUME mL 50.00
ENTER CORRECT VOLUME?

-continued

| |
|---|
| OR |
| PRESS "CLEAR" TO RECALIBRATE SYRINGE |

If the operator enters the correct volume and it is within ± 2.5% of 50 mL the system will allow infusion to proceed. If the entered volume is outside ±2.5%, or if the "clear" button is pressed, the following display appears:

| | |
|---|---|
| CALIBRATION: | |
| LOAD AN EMPTY SYRINGE | |
| ENGAGE DRIVE HEAD | |
| PRESS ENTER | "CLEAR" TO RECOMMENCE |

The controller moves the syringe actuator 7 towards the plunger until the microswitch 9 closes. The voltage reading from the potentiometer 24 is entered into EEPROM 23 in the look-up table at the diameter value closest to it. The voltage from the potentiometer 25 is entered into the look-up table and the display 13 then reads:

| | |
|---|---|
| CALIBRATION: | VOLUME mL 00.00 |
| LOAD FILLED SYRINGE | |
| ENTER VOLUME OF FLUID IN SYRINGE | |
| | "CLEAR" TO RECOMMENCE |

The controller moves the syringe actuator 7 into engagement with the plunger of the filled syringe until the switch 9 closes at which time the voltage from the potentiometer 25 is entered into EEPROM 23. The "delivery factor" resulting from the volume and position data referred to above is calculated and the display 13 reads:

| | |
|---|---|
| | VOLUME mL 50.00 |
| IS THIS A NEW INFUSION? | |
| YES/NO | |

The operator then proceeds as described above.

It should be appreciated that the infusion pump embodying the present invention is, in addition to the functions described above, also capable of performing each of the functions described in greater detail in the prior patent referred to above. Thus, for a complete understanding of the infusion pump embodying the invention, reference should be had to the description and drawings contained in the specifications of that patent.

The preferred embodiment of the drive system is designed to provide a total reduction ratio of 1000:1 in a particularly compact and simple manner from an engineering point of view. The arrangement described enables the infusion pump to deliver fluids within the range 0.1 ml/hr to 1500 ml/hr without any recoil or drive integrity problems. As a matter of comparison, commercially available infusion pumps have delivery rate ranges of the order of 0.1 ml/hr to 150 ml/hr which is insufficient for the drug infusion control system described in greater detail in the prior patent. Thus, for a given syringe size, the present drive system is capable of actuating the syringe at rates up to 10 times the rate achieved by existing devices. The particularly preferred stepper motor selected for use in the present embodiment enables adequate torque to be maintained at speed ranges up to 3000 rpm, thus facilitating the high delivery rates referred to above.

It will also be appreciated that the worm drive system described in greater detail above offers the following specific advantages:

1. Prevents reversing of the drive motor under load (as outlined in greater detail above) and renders the system effectively self locking.
2. Permits depowering of the stepper motor between steps and makes it unnecessary to hold the motor between steps, thereby reducing power drain.
3. Provides a high reduction ratio with a minimum number of components in a particularly compact manner.
4. Provides quiet operation due to continuous engagement of the toothed gears.
5. Permits the use of a stepper motor at low speeds without the necessity for shaft encoding.

In the preferred form of the invention, the use of a sprag clutch as the clutch means is desirable since its spreads the load over a large number of teeth and minimizes wear. The spring loading of the sprag clutch permits adjustment of the disengagement force to suit varying requirements. Similarly the use of a splined hub or pinion enables the sprag clutch to be suitably located and to permit disengagement of the clutch under load.

While the preferred embodiment has been described in connection with a drug infusion pump, it will be appreciated that the infusion pump and drive system will work equally well in either direction and accordingly the pump may be used to withdraw liquids as well as deliver them. For example, certain types of blood analysis require rapid withdrawal of a quantity of blood to be analysed and the drive system according to the above embodiment would enable such rapid withdrawal to be achieved. Furthermore, the pump may be used to pump fluids other than drugs.

I claim:

1. A pump for the delivery of controlled amounts of fluid from a syringe having a body and a plunger, comprising:

means for receiving and locating the body of the syringe;

syringe actuator means for engaging the plunger of the syringe held by said receiving and locating means;

means for generating a signal representing the position of said syringe actuator means;

drive means connected to said syringe actuator means for moving said plunger into said syringe body to deliver said fluid;

means for controlling said drive means;

a movable arm for contacting the body of the syringe when held by said receiving and locating means;

means for generating a signal corresponding to the position of said arm when contacting said syringe body and thus being representative of the diameter of the syringe;

memory means for storing predetermined diameter data relating to one or more syringes along with delivery factor information corresponding thereto;

logic means for determining whether the syringe diameter corresponds to one of said stored diameter data and for outputting a signal representing the result of the determination;

means responsive to a logic means output signal representing a negative determination for allowing the inputting of calibration data to said drive controlling means by storing the position of said syringe actuator means when engaged with the plunger of said syringe when empty, and storing the position of said syringe actuator means when engaged with the plunger of said syringe when full;

means for allowing a user to input the volume of said syringe;

means for calculating from said stored positions of said syringe actuator means and the volume of said syringe inputted by the user a delivery factor which is used by said drive controlling means to control the delivery of the fluid contained in said syringe at a predetermined delivery rate; and means responsive to a logic means output signal representing a positive determination for retrieving a stored delivery factor corresponding to said syringe diameter signal.

2. The pump of claim 1, wherein movement of said movable arm causes corresponding movement of an input shaft to a potentiometer to create said signal representative of the diameter of a syringe, and gear means interposed between said arm and said potentiometer to increase the number of rotations of said input shaft caused by movement of said arm.

3. The pump of claim 2, further comprising means for biasing said gear means in the direction which reduces movement of said input shaft caused by gear backlash.

4. The pump of claim 1, wherein said memory means includes a look-up table of previously stored diameter data, said calibration data being substituted for previously stored data having the closest volume value to the data being inputted.

5. The pump of claim 1, wherein said drive means comprises a motor and a drive train driven by said motor, and means for disconnecting drive coupling between said motor and said drive train to enable said syringe actuator means to be manually moved while monitoring the position of said actuator means.

6. The pump of claim 5 wherein said means for disconnecting drive coupling between said motor and said drive train comprises manually actuatable means on said syringe actuator means.

7. The pump of claim 6, wherein said manually actuatable means comprises at least one depressible lever which disengages said motor from said drive train.

* * * * *